US00PP29388P2

(12) United States Plant Patent
Van Swieten

(10) Patent No.: US PP29,388 P2
(45) Date of Patent: Jun. 12, 2018

(54) ***PHALAENOPSIS* ORCHID PLANT NAMED 'PHALYDSAP'**

(50) Latin Name: ***Phalaenopsis* hybrid**
Varietal Denomination: PHALYDSAP

(71) Applicant: ANTHURA B.V., Bleiswijk (NL)

(72) Inventor: Martinus Nicolaas Gerardus Van Swieten, Utrecht (NL)

(73) Assignee: ANTHURA B.V., Bleiswijk (NL)

( * ) Notice: Subject to any disclaimer, the term of this patent is extended or adjusted under 35 U.S.C. 154(b) by 0 days. days.

(21) Appl. No.: 15/530,596

(22) Filed: Feb. 3, 2017

(51) Int. Cl.
*A01H 5/02* (2018.01)

(52) U.S. Cl.
USPC ..... Plt./311

(58) Field of Classification Search
USPC ..... Plt./311
See application file for complete search history.

*Primary Examiner* — Susan McCormick Ewoldt
(74) *Attorney, Agent, or Firm* — Jondle & Associates, P.C.

(57) ABSTRACT

A new and distinct variety of *Phalaenopsis* plant named 'PHALYDSAP', particularly characterized by having white flowers with purple flecks and red-purple lip, 1 to 2 peduncles that are long and moderate, leaves that are oblong, and is propagated by meristem tissue culture, is disclosed.

3 Drawing Sheets

Genus and species: *Phalaenopsis* hybrid.
Variety denomination: 'PHALYDSAP'.

BACKGROUND OF THE NEW PLANT

The present invention relates to a new and distinct cultivar of *Phalaenopsis* plant, botanically known as *Phalaenopsis* hybrid of the Orchidaceae family, commonly referred to as moth orchid, and hereinafter referred to by the variety name 'PHALYDSAP'.

The new *Phalaenopsis* plant is a product of a planned breeding program conducted by the inventor in Bleiswijk, The Netherlands. The objective of this breeding program was to create a new *Phalaenopsis* plant with numerous attractive and unique white flowers with purple flecks and red-purple lip, suitable for potted plant production.

The new *Phalaenopsis* plant 'PHALYDSAP' is a result of cross-pollination made by the inventor in July 2005 in Bleiswijk, The Netherlands of the proprietary female, or seed parent, *Phalaenopsis* hybrid '01-1698' (unpatented) with the proprietary male, or pollen parent, *Phalaenopsis* hybrid '14261-01' (unpatented).

The new *Phalaenopsis* was selected by the inventor as a single plant within the progeny of the stated cross-pollination in a controlled greenhouse in Bleiswijk, The Netherlands in August 2008. Asexual reproduction of the new *Phalaenopsis* plant by meristem tissue culture since 2011 in Bleiswijk, The Netherlands, has demonstrated that the new variety reproduces true to type with all of the characteristics, as herein described, firmly fixed and retained through successive generations.

Plant Breeder's Rights for this variety have been applied for in Europe on Sep. 13, 2016. 'PHALYDSAP' has not been made publicly available or sold anywhere in the world more than one year prior to the filing date of this application.

SUMMARY OF THE INVENTION

The following are the most outstanding and distinguishing characteristics of this new cultivar when grown under normal horticultural practices in Bleiswijk, The Netherlands and can be used to distinguish 'PHALYDSAP' as a new and distinct variety of *Phalaenopsis* plant.

1) White flowers with purple flecks and red-purple lip, the number and intensity of flecks depends on the temperature;
2) 1 to 2 peduncles;
3) Peduncle is long and moderate; and
4) Shape of the leaf is oblong.

DESCRIPTION OF THE PHOTOGRAPHS

This new *Phalaenopsis* plant is illustrated by the accompanying photographs which show the overall plant habit including blooms and foliage of the plant; the colors shown are as true as can be reasonably obtained by conventional photographic procedures. The photographs were taken in a greenhouse in Bleiswijk, The Netherlands, from 50-week old plants in December 2016. Colors in the photographs may differ from the color values cited in the detailed botanical description, which accurately describe the actual colors of the new variety.

DESCRIPTION OF THE NEW VARIETY

Figure 1:
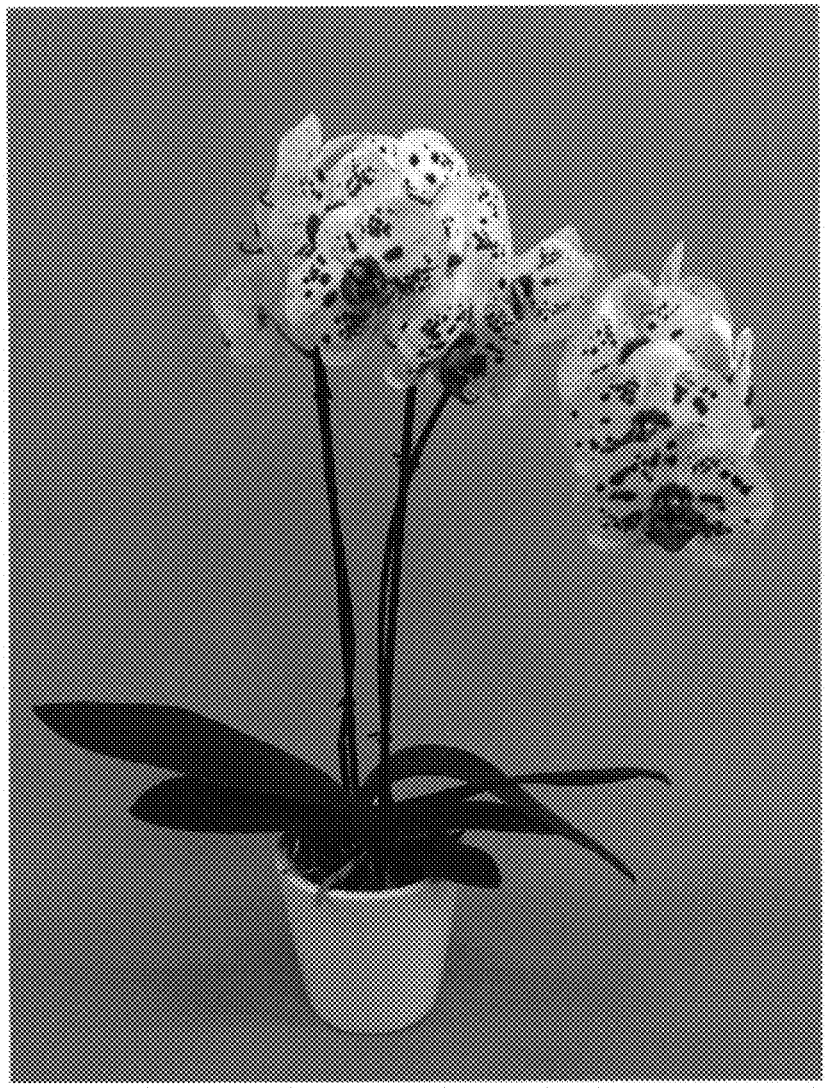
FIG. 1 shows the overall plant habit, including blooms and foliage of 'PHALYDSAP'.
Figure 2:
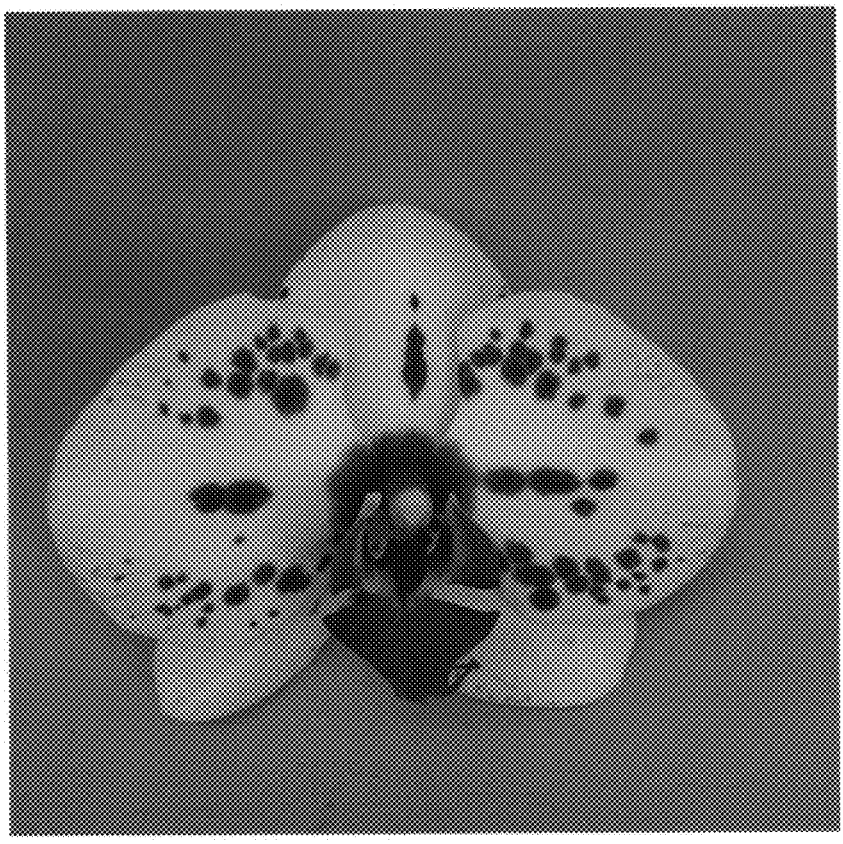
FIG. 2 shows a close-up of a flower of 'PHALYDSAP'.
Figure 3:
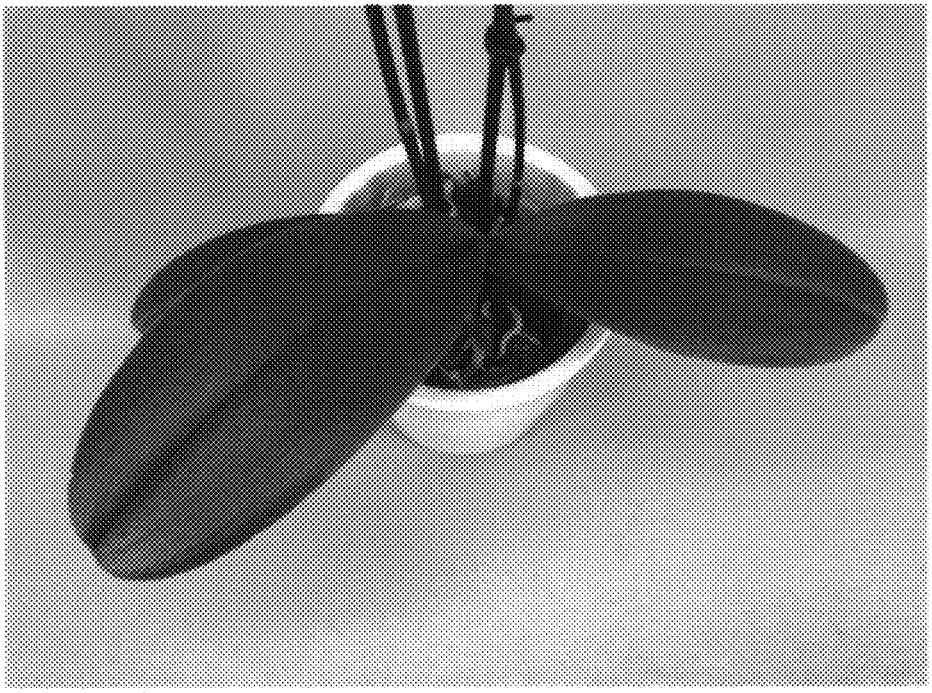
FIG. 3 shows a close-up of the leaves of 'PHALYDSAP'.

The following detailed description sets forth the distinctive characteristics of 'PHALYDSAP'. Plants of the new *Phalaenopsis* have not been observed under all possible environmental conditions. The phenotype may vary somewhat with variations in environment such as temperature, light intensity and day length, without, however, any variance in genotype. The chart used in the identification of colors described herein is The R.H.S. Colour Chart of The Royal Horticultural Society, London, England, 2015 edition, except where general color terms of ordinary significance are used. The color values were determined under 4000-

6000 lux natural light in a greenhouse in Bleiswijk, The Netherlands. Observations and measurements were made in December 2016 on 50-week old plants which were planted from a nursery tray in 12 centimeter (diameter) pots and grown in a greenhouse between 27° C. to 29° C. for 30 weeks, continued by a cooling period of 8 weeks between 18° C. to 20° C. and 12 weeks in a greenhouse of 21° C.

DETAILED BOTANICAL DESCRIPTION

Classification:

*Family*.—Orchidaceae.

*Botanical*.—*Phalaenopsis* hybrid.

*Common name*.—Moth orchid.

*Variety name*.—'PHALYDSAP'.

Parentage:

*Female parent*.—*Phalaenopsis* cultivar '01-1698' (unpatented).

*Male parent*.—*Phalaenopsis* cultivar '14261-01' (unpatented).

Propagation:

*Type*.—Meristem tissue culture.

Roots:

*Root description*.—Greyed-green colored roots (RHS 190B/C) with branching lateral roots having greyed-green tips (RHS 195B).

Plant:

*Commercial crop time to flowering*.—Approximately 48 to 50 weeks from a rooted cutting to finish in a 12 cm pot.

*Growth habit of peduncle*.—Standard, green leaves, raceme to panicle.

*Height* (*from soil level to top of inflorescence*).—Approximately 49.0 cm to 59.0 cm.

*Width* (*measured from leaf tips*).—About 29.0 cm to 34.0 cm.

*Vigor*.—Moderate.

Leaves:

*Mature leaves*.—Quantity per plant: 6 to 8 leaves are produced before flowering. Length (fully expanded): 16.0 cm to 18.0 cm. Width: 7.0 cm to 8.0 cm. Shape: Oblong. Base shape: Moderately elongated. Apex: Unequal obtuse. Leaf blade angle with the petiole (measured from the horizontal position): Between 10 degrees and 25 degrees. Leaf margin: Entire. Color: Upper surface: RHS 146A. Lower surface: RHS 146B. Texture: Smooth. Thickness: 2.3 mm to 2.8 mm. Venation: Pattern: Parallel. Color of the midvein: Upper surface: RHS 146A. Lower surface: RHS 146B.

Peduncle:

*Quantity per plant*.—1 to 2.

*Number of flowers per peduncle*.—8 to 12.

*Length*.—51.0 cm to 56.0 cm.

*Diameter*.—4.9 mm to 5.1 mm.

*Strength*.—Moderate.

*Aspect*.—Upright to slightly pendant.

*Texture*.—Smooth.

*Color*.—Mix of light brown (RHS N199A) and green (RHS 146B).

*Internode length*.—65.0 mm to 75.0 mm.

*Callosities*.—None.

Inflorescence description:

*Appearance*.—Upright to slightly pendant, raceme to panicle inflorescence with bilaterally symmetrical flowers that open in succession beginning with the lowermost flower.

*Inflorescence size*.—Height (from base to tip): 210.0 mm to 230.0 mm.

*Flowering time*.—First flowers can be expected 10 to 11 months after planting in a 12 cm (diameter) pot.

*Flower*.—Height: 72.0 mm to 74.0 mm. Diameter: 82.0 mm to 84.0 mm. Depth of lip: 19.0 mm to 21.0 mm.

*Flower longevity*.—On the plant: 7 to 12 weeks.

*Fragrance*.—Absent.

*Flower bud*.—Average size: Large. Length: 23.0 mm to 25.0 mm. Width: 21.0 mm to 23.0 mm. Shape: Egg shaped. Color: Green (RHS 144C) with a few fading flecks at the base (RHS N79A) and a little red-purple shade (RHS 186B).

*Petals*.—Arrangement: Open/free. Shape: Semi-circular. Apex: Rounded to slightly obtuse asymmetric. Margin: Slightly undulated. Length (from base to tip): 38.0 mm to 40.0 mm. Width: 44.0 mm to 46.0 mm. Color (when fully opened): Upper surface: Basic color: White (RHS NN155C). Over color: Purple flecks (RHS 187B and N79C). Lower surface: Basic color: White (RHS NN155C). Over color: Fading purple flecks (RHS N79B).

*Dorsal sepal*.—Shape: Broad elliptic. Apex: Obtuse asymmetric. Margin: Entire. Length (from base to tip): 41.0 mm to 43.0 mm. Width: 33.0 mm to 35.0 mm. Color (when fully opened): Upper surface: Basic color: White (RHS NN155C). Over color: Purple flecks (RHS 187B and N79C). Lower surface: Basic color: White (RHS NN155C). Over color: Slightly light green (RHS 145D) and light purple (RHS N78D) in the middle; fading dots (RHS N79B).

*Lateral sepals*.—Shape: Ovate. Apex: Obtuse asymmetric. Margin: Entire. Length (from base to tip): 42.0 mm to 44.0 mm. Width: 29.0 mm to 31.0 mm. Color (when fully opened): Upper surface: Basic color: White (RHS NN155C). Over color: Light green at the base (RHS 145C/D); purple flecks (RHS 187B and N79C). Lower surface: Basic color: White (RHS NN155C). Over color: Light green at the base (RHS 145C) and light purple shade (RHS N78D); fading purple flecks (RHS N79B).

*Labellum* (*lip*).—Whiskers: Present. Length of whiskers: 11.0 mm to 13.0 mm. Color of whiskers: Red-purple (RHS 71A and 61A) with white tip (RHS NN155C). Pubescence on the lip: Absent.

*Lateral lobe*.—Shape: Type V (as described in the International Union for the Protection of New Varieties of Plants (UPOV) Test Guidelines for *Phalaenopsis*); spatulate. Margin: Slightly undulated. Length: 19.0 mm to 21.0 mm. Width: 13.0 mm to 15.0 mm. Color: White (RHS NN155C) with dark red flecks (RHS 187B) at the base; red (RHS 185A) and purple toward the edge (RHS N78A).

*Apical lobe*.—Shape: Triangular. Margin: Entire. Length: 21.0 mm to 23.0 mm. Width: 23.0 mm to 25.0 mm. Color: Red (RHS 185A) at the base with yellow flecks toward the callus (RHS 5B); purple toward the whiskers (RHS NN78B).

*Callus*.—Average size: Medium. Height: 0.5 cm to 0.6 cm. Length: 0.5 cm to 0.6 cm. Width: 0.4 cm to 0.5 cm. Color: Dark red (RHS 187A).

*Reproductive organs*.—Column: Length: 9.0 mm to 11.0 mm. Diameter: 5.1 mm to 5.6 mm. Color: Purple (RHS N78A) with darker purple region in the middle (RHS N79C). Pollinia: Quantity: 2. Diameter: 1.0 mm to 1.1 mm. Color: Yellow-orange (RHS 17A). Ovary: Length: 6.0 mm to 8.0 mm. Diameter: 2.1 mm to 2.3 mm. Pedicel: Length: 31.0 mm to 33.0 mm. Diameter: 2.5 mm to 2.8 mm. Color: Light green (RHS 145B/C) and light purple (RHS N78D) towards the flower.

Disease, pest, and stress resistance: No specific resistance or susceptibility observed to pathogens and pests common to *Phalaenopsis*.

Fruit and seeds: Fruit and seed development has not been observed on plants of the new *Phalaenopsis*.

COMPARISON WITH PARENTAL AND COMMERCIAL VARIETIES

The female parent plant of 'PHALYDSAP', cultivar '01-1698' (unpatented), is no longer in existence, so a meaningful comparison cannot be made.

'PHALYDSAP' differs from male parent plant '14261-01' (unpatented) in that 'PHALYDSAP' has white, flecked flowers with purple centers and a dark red callus, whereas '14261-01' has light purple flowers with white centers and a yellow, dotted callus. Additionally, 'PHALYDSAP' has smaller flowers and shorter whiskers than '14261-01'.

'PHALYDSAP' is most similar to the commercial *Phalaenopsis* plants named 'PHALIFSIB' (U.S. Plant Pat. No. 27,459) and 'PHALFUNEL' (unpatented). 'PHALYDSAP' differs from the commercial variety 'PHALIFSIB' in that 'PHALYDSAP' has an apical lobe with red at the base, yellow flecks toward the callus and purple toward the whiskers, red-purple whiskers with white tips, and a purple column with darker purple region in the middle, whereas 'PHALIFSIB' has a white apical lobe with yellow-green wings and a stripe in the middle and a brown edge at the base, white whiskers with yellow tips, and a white column. Additionally, 'PHALYDSAP' has smaller flowers than 'PHALIFSIB'.

'PHALYDSAP' differs from the commercial variety 'PHALFUNEL' in that 'PHALYDSAP' has an apical lobe with red at the base, yellow flecks toward the callus and purple toward the whiskers, red-purple whiskers with white tips, and a purple column with darker purple region in the middle, whereas 'PHALFUNEL' has a white apical lobe with yellow wings and a stripe in the middle, white whiskers with yellow tips, and a white column. Additionally, 'PHALYDSAP' has smaller flowers than 'PHALFUNEL'.

I claim:

1. A new and distinct variety of *Phalaenopsis* plant named 'PHALYDSAP', substantially as described and illustrated herein.

* * * * *